US010130325B2

(12) United States Patent
Launay et al.

(10) Patent No.: US 10,130,325 B2
(45) Date of Patent: Nov. 20, 2018

(54) SYSTEM AND METHOD OF CORRECTING BANDING ARTIFACTS IN CARDIAC CT

(71) Applicant: General Electric Company, Schenectady, NY (US)

(72) Inventors: Laurent Launay, Buc (FR); Darin R. Okerlund, Waukesha, WI (US); Guillermo Ruiz, Buc (FR); Brian E. Nett, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 727 days.

(21) Appl. No.: 14/294,504

(22) Filed: Jun. 3, 2014

(65) Prior Publication Data
US 2014/0362970 A1 Dec. 11, 2014

Related U.S. Application Data

(60) Provisional application No. 61/833,227, filed on Jun. 10, 2013.

(51) Int. Cl.
*A61B 6/03* (2006.01)
*G06T 3/00* (2006.01)
(Continued)

(52) U.S. Cl.
CPC ............ *A61B 6/5241* (2013.01); *A61B 6/504* (2013.01); *A61B 6/5235* (2013.01);
(Continued)

(58) Field of Classification Search
CPC .... A61B 6/00; A61B 6/02; A61B 6/03; A61B 6/032; A61B 6/486; A61B 6/504; A61B 6/52; A61B 6/5211; A61B 6/5217; A61B 6/5229; A61B 6/5235; A61B 6/5241; A61B 6/5258; A61B 6/5288; G06F 19/00; G06F 19/30; G06F 19/34; G06T 3/00; G06T 3/0068; G06T 3/0075; G06T 5/00; G06T 5/50; G06T 7/00; G06T 7/0002; G06T 7/0012; G06T 7/0014; G06T 7/0016; G06T 7/0022; G06T 7/0024; G06T 7/0028; G06T 7/0038; G06T 7/004; G06T 7/0042; G06T 7/0051; G06T 7/0065; G06T 7/0067; G06T 7/0079; G06T 7/0097; G06T 11/00; G06T 11/003; G06T 11/005; G06T 2207/00; G06T 2207/10; G06T 2207/10072; G06T 2207/10081; G06T 2207/20;
(Continued)

(56) References Cited

U.S. PATENT DOCUMENTS 6,195,445 B1 * 2/2001 Dubuisson-Jolly ........................ G06K 9/3216
382/107
6,526,117 B1 * 2/2003 Okerlund ............... A61B 6/032
378/4
(Continued)

*Primary Examiner* — Anastasia Midkiff
(74) *Attorney, Agent, or Firm* — Fletcher Yoder, P.C.

(57) ABSTRACT

A CT system includes a gantry having a rotatable base and having an opening for receiving an object to be scanned, an x-ray source, a CT detector, and a computer programmed to detect a mis-registration at a slab boundary between a first slab and a second slab of a reconstructed image, quantify an amount of mis-registration at the slab boundary, and adjust the reconstructed image at the slab boundary based on the quantification.

17 Claims, 6 Drawing Sheets

(51) Int. Cl.
*G06T 5/50* (2006.01)
*G06T 7/00* (2017.01)
*G06K 9/20* (2006.01)
*G06K 9/56* (2006.01)
*G06K 9/62* (2006.01)
*G06K 9/78* (2006.01)
*A61B 6/00* (2006.01)
*G06K 9/46* (2006.01)
G06T 11/00 (2006.01)
G06T 5/00 (2006.01)
A61B 6/04 (2006.01)

(52) U.S. Cl.
CPC .......... *A61B 6/5258* (2013.01); *A61B 6/5288* (2013.01); *G06K 9/4638* (2013.01); *G06K 9/6204* (2013.01); *G06T 3/0068* (2013.01); A61B 6/032 (2013.01); A61B 6/0457 (2013.01); A61B 6/486 (2013.01); A61B 6/503 (2013.01); A61B 6/5264 (2013.01); G06K 9/56 (2013.01); G06K 9/6202 (2013.01); G06K 9/6203 (2013.01); G06K 9/78 (2013.01); G06K 2009/2045 (2013.01); G06T 5/002 (2013.01); G06T 7/0016 (2013.01); G06T 11/008 (2013.01); G06T 2207/10081 (2013.01); G06T 2207/20221 (2013.01); G06T 2207/20228 (2013.01); G06T 2207/30048 (2013.01); G06T 2207/30101 (2013.01); G06T 2207/30112 (2013.01); G06T 2211/404 (2013.01)

(58) Field of Classification Search
CPC . G06T 2207/20092; G06T 2207/20096; G06T 2207/20101; G06T 2207/20212; G06T 2207/20221; G06T 2207/20228; G06T 2207/30; G06T 2207/30004; G06T 2207/30101; G06T 2207/30172; G06T 2210/00; G06T 2210/41; G06T 2211/00; G06T 2211/40; G06T 2211/404; G06K 9/00; G06K 9/20; G06K 9/2054; G06K 9/2063; G06K 9/32; G06K 9/3216; G06K 9/34; G06K 9/344; G06K 9/36; G06K 9/46; G06K 9/4604; G06K 9/4609; G06K 9/4638; G06K 9/54; G06K 9/56; G06K 9/60; G06K 9/62; G06K 9/6201–9/6204; G06K 9/6288; G06K 9/629; G06K 9/78; G06K 2009/2045; G06K 2009/3291; G06K 2009/363; G06K 2009/6213
See application file for complete search history.

(56) References Cited

U.S. PATENT DOCUMENTS

| | | | |
|---|---|---|---|
| 6,754,376 B1 | 6/2004 | Turek et al. | |
| 6,829,379 B1* | 12/2004 | Knoplioch | A61B 6/469 382/131 |
| 6,968,032 B2 | 11/2005 | Mohr et al. | |
| 7,010,149 B1 | 3/2006 | Knoplioch et al. | |
| 7,191,101 B2 | 3/2007 | Knoplioch et al. | |
| 7,558,417 B2 | 7/2009 | Knoplioch et al. | |
| 7,636,462 B2 | 12/2009 | Li et al. | |
| 7,639,855 B2* | 12/2009 | Matsumoto | G06T 7/60 382/131 |
| 8,224,056 B2 | 7/2012 | Pack et al. | |
| 2005/0135554 A1* | 6/2005 | Mohr | A61B 6/032 378/19 |
| 2007/0127797 A1 | 6/2007 | Angelos et al. | |
| 2010/0061601 A1* | 3/2010 | Abramoff | G06K 9/00617 382/117 |
| 2011/0142313 A1* | 6/2011 | Pack | G06T 7/0081 382/131 |
| 2012/0134550 A1 | 5/2012 | Knoplioch et al. | |
| 2013/0051643 A1 | 2/2013 | Jackson et al. | |
| 2013/0077749 A1* | 3/2013 | Akahori | A61B 6/486 378/62 |
| 2013/0114790 A1* | 5/2013 | Fabrizio | A61B 6/02 378/62 |
| 2014/0249791 A1* | 9/2014 | Taylor | A61B 5/02007 703/11 |

* cited by examiner

SYSTEM AND METHOD OF CORRECTING BANDING ARTIFACTS IN CARDIAC CT

CROSS-REFERENCE TO RELATED APPLICATION

The present application claims priority to U.S. Provisional Application 61/833,227 filed Jun. 10, 2013, the disclosure of which is incorporated herein in its entirety.

BACKGROUND

This disclosure relates generally to diagnostic imaging and, more particularly, to an improved method of post processing reconstructed CT images to improve vessel mis-registration and greyscale de-banding between slabs within a CT image.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. CT detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

Cardiac imaging data is obtained by rotating the CT detector about the heart, in either an axial or a helical scan, and obtaining the data during the rotational process. However, many systems (new or legacy) typically do not include a detector that has an axial length that is greater than that of the heart. As such, to obtain full cardiac images, typically several rotations of the detector occur to cover the full axial length of the heart.

Since the introduction of Cardiac CT imaging, the presence of banding artifacts has been one of the limitations of the technology. These artifacts appear as horizontal shifts in multiplanar or 3D images. They can affect all structures in the images, but are most problematic on coronaries as they can show an artificial "rupture" in the vessel. Although the diagnostic remains most the times possible by looking at both "sides" of the vessel individually, the artifacts often create complaints from the customers as it makes vessel visualization and reporting more difficult. Embodiments disclosed allow better visualization and assessment of the vessels, and help the customer create report images where the artifacts are compensated.

In a typical imaging session, cardiac imaging data may be obtained over perhaps 3-4 heartbeats. The number of heartbeats over which data is acquired is dependent on such factors as the axial length of the heart, the axial length of the detector, the rotational speed of the detector about the heart, and the heart rate, as examples. Thus, in an example where data from 3 heartbeats is used to reconstruct an image of the heart, images are thereby reconstructed as separate "slabs", that are then combined to form the total cardiac image volume. That is, slabs of data are reconstructed wherein each slab is from data within a given heartbeat, and the slabs are joined together along the axial direction to form a complete image volume of the heart. As such, as the detector rotates and the heart continues to beat, imaging data is obtained over a number of heartbeats, and data obtained during each heartbeat is reconstructed into respective images.

However, for a variety of reasons, various types of imaging artifacts can occur. For instance: 1) in-plane and/or slice-to-slice coronary motion can occur within a slab; 2) spatial misalignments can occur at the slab boundary (causing vessels to be mis-registered); and 3) Hounsfield Unit (HU) non-uniformity can occur at the slab boundary as well. That is, between slabs and generally within imaged areas that are removed from the vessel region, greyscale non-uniformity can occur that causes boundaries between slabs to be visible (although such non-uniformity may be merely aesthetic and may not affect a diagnosis, HU non-uniformity correction may nevertheless be applied to minimize or remove the visible boundary between slabs).

Known techniques may be employed to correct the first 1) of the artifacts—in-plane and/or slice-to-slice coronary motion can occur within a slab.

For instance, in one known method in-plane and slice-to-slice motion may be corrected by using filters applied to identified regions of interest to generate a sequence of filtered images. Each of the filtered images in the generated sequence of filtered images includes data acquired near a different reference point, and therefore a motion path corresponding to each region of interest is determined based on one or more correspondences in the sequence of filtered images.

Another known method to correct in-plane and slice-to-slice motion includes reconstructing initial images on which to perform an image correction, and generating an image correction request for the images identified for image correction, with the image correction request specifying a processing operation to be performed on the respective images. The reconstructed initial images are transferred to a separate workstation that automatically initiates the image correction upon verifying a presence of an image correction request on the initial images so as to generate corrected images.

However, image artifacts can include aspects of all three the three artifacts 1)-3). That is, not only can in-plane and/or slice-to-slice coronary motion occur within a slab, but vessel mis-registration can occur at boundaries between slabs due to a number of elements that include but are not limited to inadequate temporal resolution, heartbeat to heartbeat variability, non-repeatable beat-to-beat heart motion, patient motion (patient moving on the table, patient breathing, etc.), and table mis-alignment, as examples. Hounsfield Unit (HU) non-uniformity can occur at the slab boundary as well.

Thus, there is a need to improve vessel mis-registration and greyscale de-banding between slabs within a CT image.

BRIEF DESCRIPTION

Embodiments are directed toward a method and apparatus to reduce vessel mis-registration and improve greyscale de-banding between slabs in images in a CT system.

According to one aspect, a CT system includes a gantry having a rotatable base and having an opening for receiving an object to be scanned, an x-ray source, a CT detector, and a computer programmed to detect a mis-registration at a slab boundary between a first slab and a second slab of a reconstructed image, quantify an amount of mis-registration at the slab boundary, and adjust the reconstructed image at the slab boundary based on the quantification.

According to another aspect, a method of CT imaging includes detecting a mis-registration between a first slab and a second slab of a reconstructed image, quantifying an amount of mis-registration between the first and second slabs, and adjusting the reconstructed image in the first and second slabs based on the quantification.

According to yet another aspect, a non-transitory computer-readable medium tangibly embodying computer-executable instructions that cause the computer to detect a mis-registration at a slab boundary between first and second slabs of a reconstructed image, quantify an amount of mis-registration at the slab boundary, and adjust the reconstructed image at the slab boundary based on the quantification.

Various other features and advantages will be made apparent from the following detailed description and the drawings.

BRIEF DESCRIPTION OF THE DRAWINGS

The disclosed materials may be implemented in an imaging system such as a CT system. Following are descriptions of various figures.

DETAILED DESCRIPTION

Disclosed is a post-processing approach which reduces cardiac CT banding artifacts by focusing on the coronary arteries. The disclosed process provides a dedicated post-processing filter that the user can switch ON or OFF to compensate for the banding artifacts on a given vessel. The filter will leverage the centerline used to visualize the vessel to detect potential slab-to-slab misalignments artifact, quantify it, and eventually compensate for it with vessel-centered local deformation. Additionally/subsequently, the "seam artifact" that can occur at a slab-to-slab boundary is minimized with an adaptive greyscale de-banding technique that preserves the integrity of the vessel, avoiding the possibility of creating new artifacts within/near the vessel due to the greyscale debanding correction itself (that could be misinterpreted as a pathology).

The operating environment of disclosed embodiments is described with respect to a sixty-four-slice computed tomography (CT) system. However, it will be appreciated by those skilled in the art that embodiments of the invention are equally applicable for use with other multi-slice configurations. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
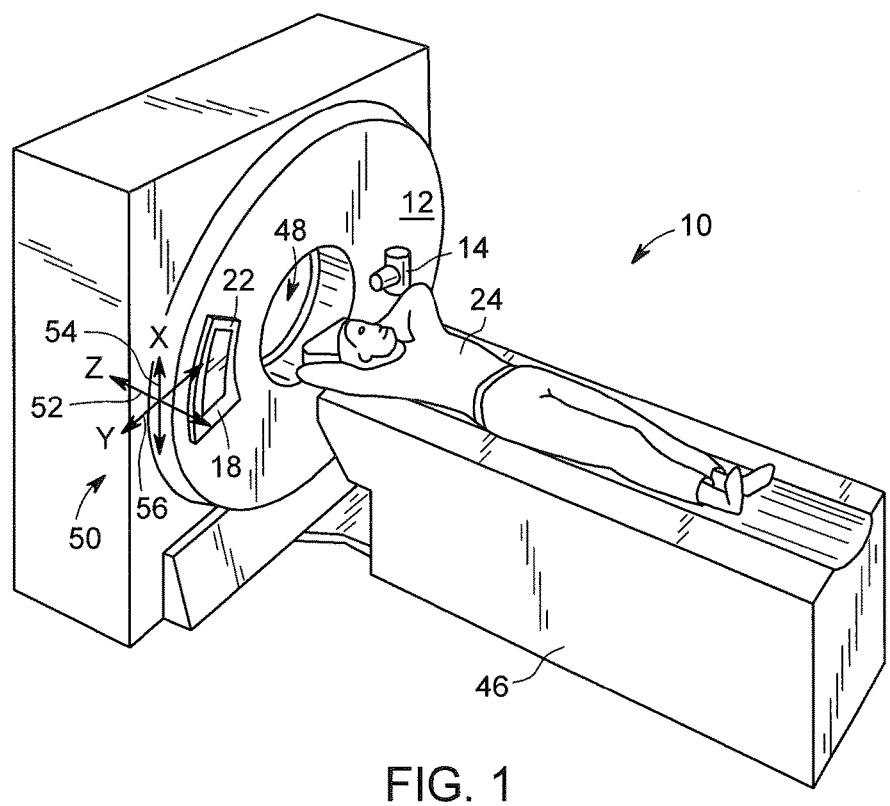
FIG. 1 is a pictorial view of a CT imaging system that incorporates embodiments of the invention.
Figure 2:
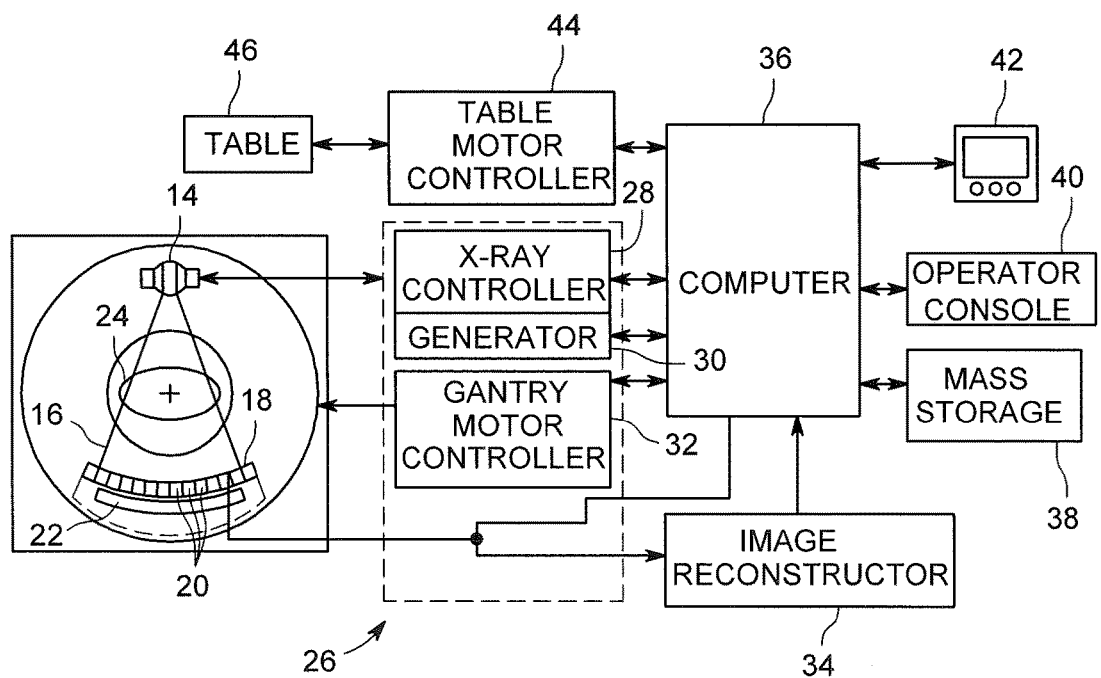
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 and data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray source 14 to detector assembly 18.

X-ray source 14, in accordance with present embodiments, is configured to emit x-rays or x-ray beam 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kV, 120 kVp, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Figure 3:
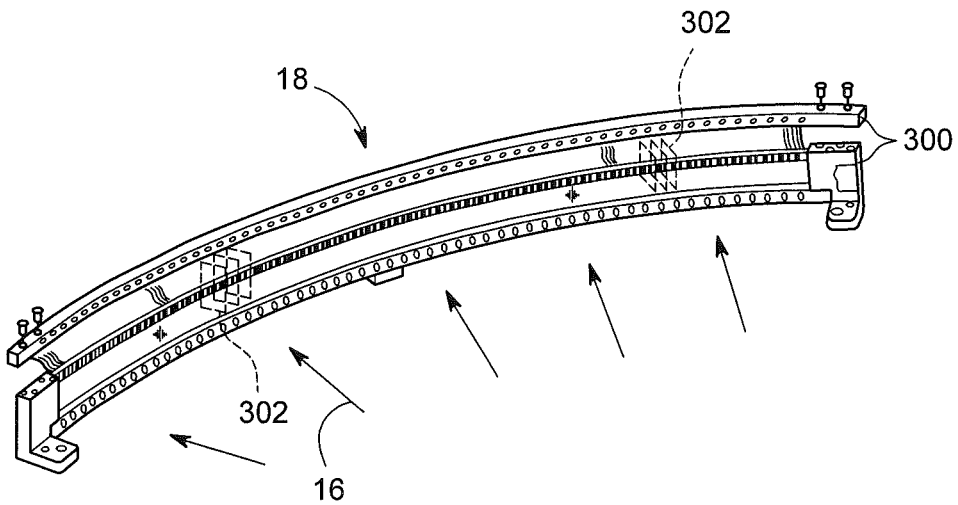
FIG. 3 is a perspective view of one embodiment of a CT system detector array.

As shown in FIG. 3, a typical detector assembly 18 includes rails 300 having collimating blades or plates 302 placed therebetween. Plates 302 are positioned to collimate x-rays 16 before such beams impinge upon, for instance, detector 20 of FIG. 4 positioned on detector assembly 18. In one embodiment, detector assembly 18 includes fifty-seven detectors or detector modules 20, each detector 20 having an array size of 64×16 of pixel elements 400. As a result, detector assembly 18 has sixty-four rows and nine hundred twelve columns (16×57 detectors) which allows sixty-four simultaneous slices of data to be collected with each rotation of gantry 12. Rails 300 are mounted to a plate that is vertically mounted in gantry 12. Z-axis 52 therefore extends orthogonal to the mounting plate such that rails 300 extend axially and at a distance from the mounting plate. Thus, as detectors grow in z-direction 52, so too does the cantilever distance.

Figure 4:
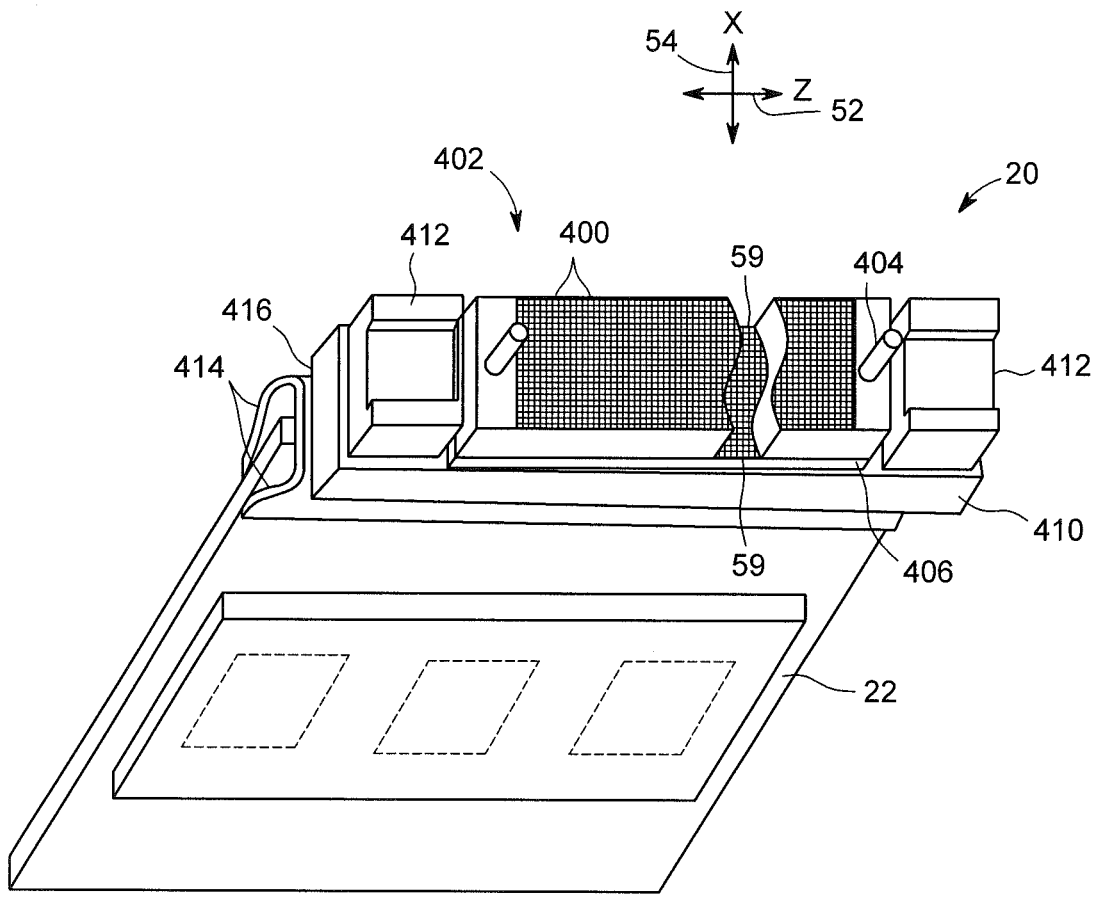
FIG. 4 is a perspective view of one embodiment of a detector.

Referring to FIG. 4, detector 20 includes DAS 22, with each detector 20 including a number of detector elements 400 arranged in pack 402, and having a width that corresponds to the cantilever length shown in FIG. 3. Detectors 20 include pins 404 positioned within pack 402 relative to detector elements 400. Pack 402 is positioned on a backlit diode array 406 having a plurality of diodes 59. Backlit diode array 406 is in turn positioned on multi-layer substrate 410. Spacers 412 are positioned on multi-layer substrate 410. Detector elements 400 are optically coupled to backlit diode array 406, and backlit diode array 406 is in turn electrically coupled to multi-layer substrate 410. Flex circuits 414 are attached to face 416 of multi-layer substrate 410 and to DAS 22. Detectors 20 are positioned within detector assembly 18 by use of pins 404.

Figure 5:
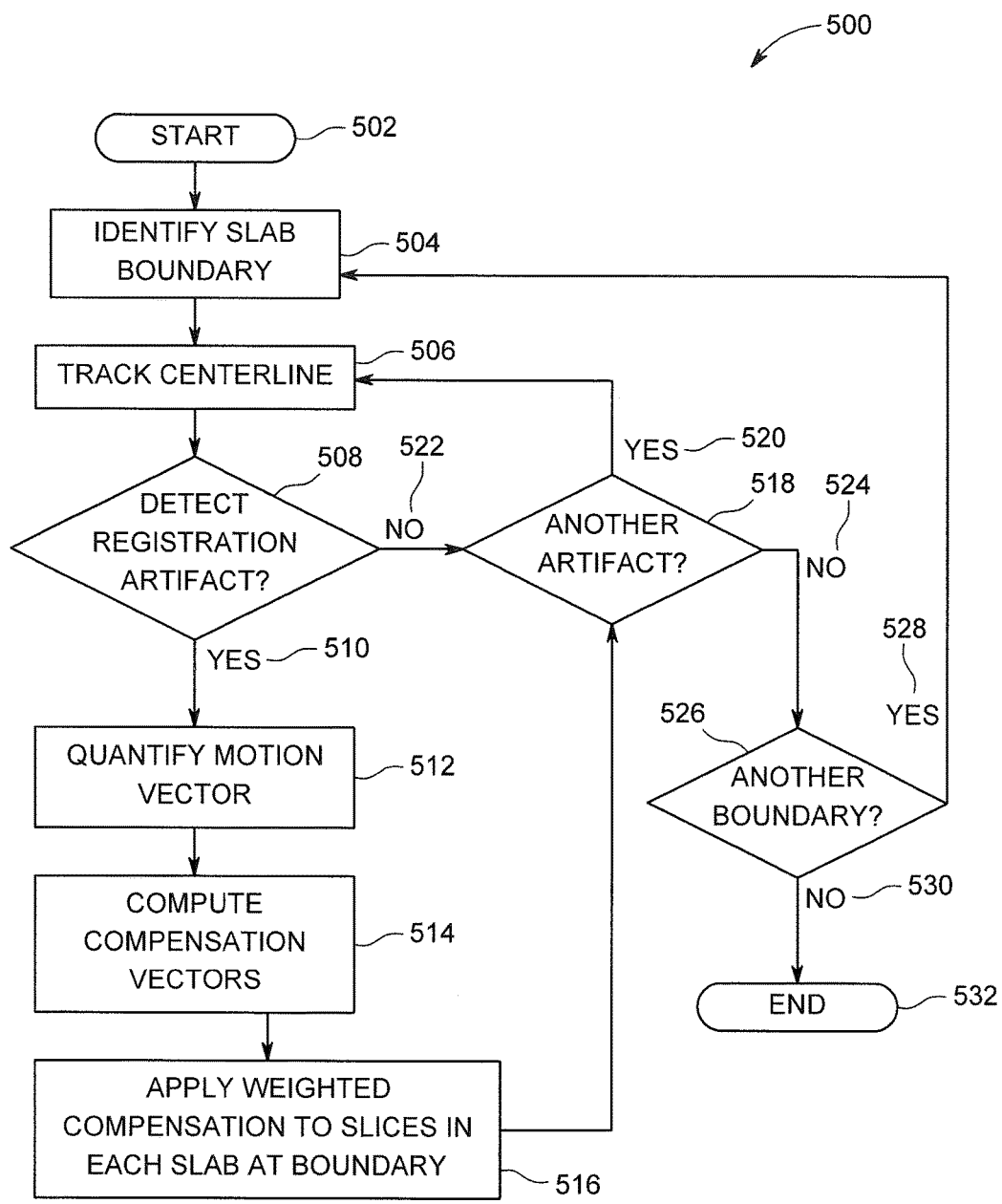
FIG. 5 illustrates a method of vessel registration correction, according to one embodiment.

Referring to FIG. 5, vessel registration correction 500 is implemented in the following steps. Starting at step 502, a slab boundary is identified at step 504. The centerline of the vessel is tracked at step 506. Correction 500 can either be totally automated in the background, or initiated explicitly by the customer during visualization. Correction 500 can also result from a manually tracked vessel centerline that is performed by the customer or user. The correction is based on an assumption that the banding artifact introduces limited distortion on the centerline. If the centerline is distorted, other steps can be added to compensate for the distortion. At step 508, the location of the banding or registration artifact is sought by finding two adjacent slices which are not reconstructed based on data from the same heartbeat (i.e., the location of a slab boundary), and therefore are candidates for having an artifact. This operation can usually be performed based on the digital and communication (DICOM) information provided by the CT scanner. If this information is not available, an alternate implementation could be to detect the artifact location by a motion estimation using other known techniques to determine slice-to-slice coronary motion. If a mis-registration artifact is detected 510, then the magnitude of artifact is quantified for the coronary artery at step 512.

Because the artifact is linked to the fact the vessel location may not be exactly the same between the two adjacent slices at a slab boundary (i.e., at different heart beats), the artifact is simply quantified as the motion vector (tx, ty) in the axial plane. This vector is obtained by A) computing intersection points I1 and I2 between the vessel centerline and the 2 slices or planes, and B) maximizing a simple cross-correlation metric, computed in a small window centered around I1 and I2. Two compensation vectors (cx, cy) and (−cx, −xy) are computed at step 514, which represent the motion to apply to the vessel on each slice to "re-center" it on the vessel centerline. This is obtained by A) computing a "normal" displacement (nx, ny) of the vessel between the two slices on either side of the slab boundary, which is due to the angle between the vessel and the horizontal plane. This can be obtained based on the centerline itself, or by computing the motion vector on adjacent slices (not impacted by the artifacts), with the technique described in step 212, and averaging the value obtained on both sides. B) Splitting the "real" motion in two: cx=(tx−nx)/2; and cy= (ty−ny)/2, and applying as a shift. At step 516 a weighted and decreasing compensation vector for X slices on each side of the artifact (X=5 in one example). In one example the compensation vector is applied linearly in a decreasing fashion from the slab boundary, but according to embodiments, other than a linear application (polynomial, power function, logarithmic function, etc. . . . ) may be applied.

A non-linear warping may be applied to all the 2×X slices based on the compensation vector, with following steps: Compute the intersection Is between the centerline and current slice using 2 diameters D1 and D2, create a deformation field such as Deformation in null for all points at a distance to Is greater than D2 Deformation, that is equal to the compensation vector of the slice for all points at a distance lower than D1 Deformation, and decreases linearly for points between D1 and D2. Further, correction within each slice in its weighted form is not globally applied, but is decreasingly applied in a footprint within each slice that is, in one example, a 20 mm diameter surrounding the artifact. Accumulation of the warped 2D images may create a warped 3D Volume which is simply displayed in place of the original volume when the filtered is switched ON. The process may be repeated for all vessels.

At step 518 the boundary is assessed for additional registration artifacts and, if found 520, then control returns to step 506 to track the centerline of the mis-registration. Also, at step 508, if no registration artifact is detected 522, control moves to step 518 to assess if another artifact is detected at the current boundary. If not, 524, then control returns to step 526 to determine if another boundary is present (that is, if the present boundary is the last one for assessment or not). If another boundary is present 528, then control returns to step 504 to identify the slab boundary. Control again passes through step 506 to step 508 and, when no further registration artifact is detected 522, then control passes to step 526. Once no boundary is found 530, then the process ends at step 532.

Figure 6:
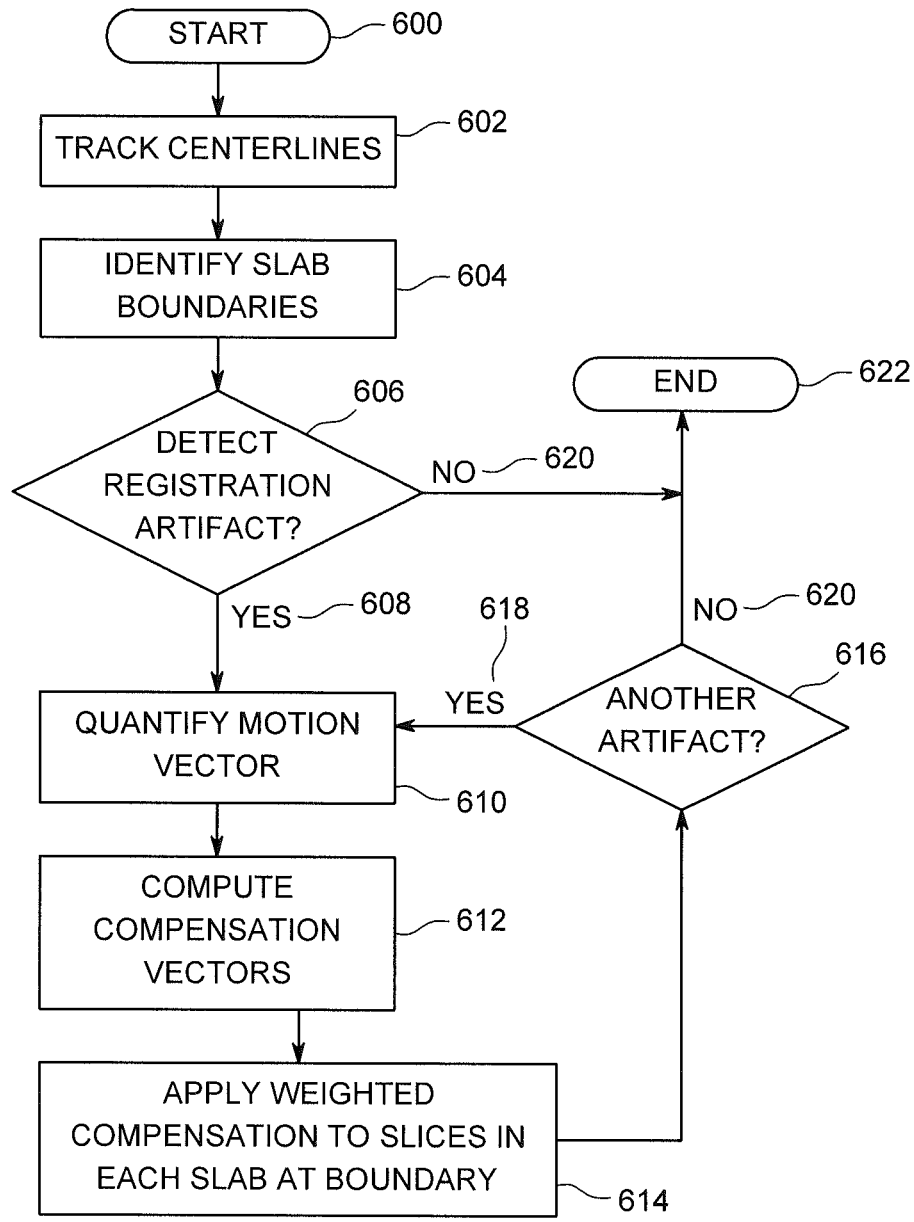
FIG. 6 illustrates a method of tracking globally the coronary vessel centerlines within the image, according to one embodiment.

According to another embodiment and consistent with the steps of FIG. 5, referring to FIG. 6, starting at step 600, coronary vessel centerlines within the image can be tracked globally. At step 602, centerlines are tracked and at step 604 slab boundaries are identified within the image volume to be corrected. Mis-registration artifacts are searched for at step 606, and if detected 608, they are quantified at step 610, a compensation vector is determined at step 612, and a weighting correction is applied at step 614 and as described with respect to FIG. 5 above. Mis-registration artifacts are searched for at step 616, and if detected 618, then the process repeats. However, if not detected 620, then the process ends at step 622. Thus, centerlines can be tracked and for each slab boundary location, if a mis-registration artifact is detected (which can also be referred to as a registration artifact) at the slab boundary and at its intersection with the vessel centerline, then the steps to quantify, compute, and compensate can be applied.

Vessel mis-registration correction can be implemented as a simple post-processing feature which can be switched on and off. This can then be presented as a simple extension of existing visualization features specialized for banding artifacts. It also enables the user to manually modify the centerline before the de-banding for more difficult cases. In an alternate implementation, this disclosed subject matter could also be applied as part of an automatic processing chain to generate a set of corrected images. It can also be easily combined with coronary motion correction technology to provide images both corrected for motion and for banding artifacts. Utilizing an embodiment that includes up front coronary motion correction, the performance of debanding may be even more effective as it can start with well-defined, non-blurry vessels contained within the input image volume. i.e., it is more conducive to register two "sharp"/"crisp" structures (vessels) with well-defined extent than to register two blurry, poorly defined structures.

In addition, this post processing solution is compatible with numerous acquisition/reconstruction modes: dual-energy and conventional acquisition, helical and axial step-and-shoot, standard and high-resolution acquisition. As such, it is contemplated that banding artifacts may be reduced by offering a solution other than a system having full organ coverage, and using a wide detector brute-force hardware approach.

In one embodiment, following deformable vessel registration, one step is done where a localized blending across heart cycles can then be applied to reduce HU gray scale no uniformities (due to differences in iodine contrast level, etc.) and apparent "seams" in the datasets. That is, HU grayscale mismatch may occur between slab boundaries.

Figure 7:
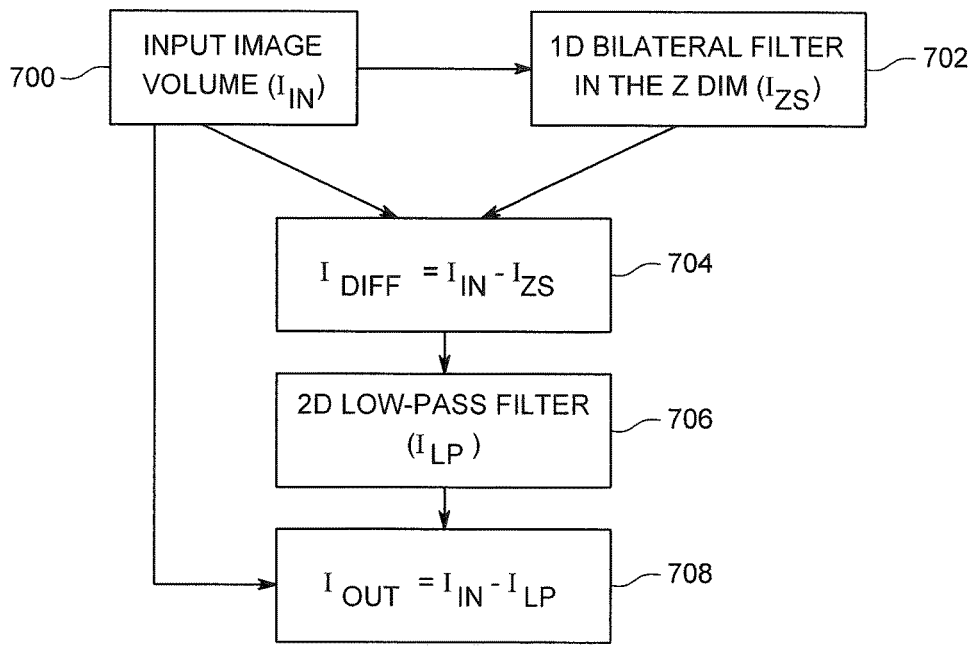
FIG. 7 illustrates a high level diagram of a gray scale filter, according to one embodiment.

Referring to FIG. 7, a high level diagram of a gray scale filter is shown. The basic flow is that the input volume 700 is input to a 1D bilateral filter 702 in the z dimension which aims to smooth the boundary between slabs while preserving high contrast changes such as vessels.

For each boundary location the same operations are performed. The first step is to determine the slices to process for the given boundary. Care is taken to touch fewer slices when the boundary slabs are small. That is, the number of slices is obtained, and a mathematical algorithm is arranged to step through each slice while performing the relevant calculations, ensuring to carry forth and index element references between slices.

Figure 8:
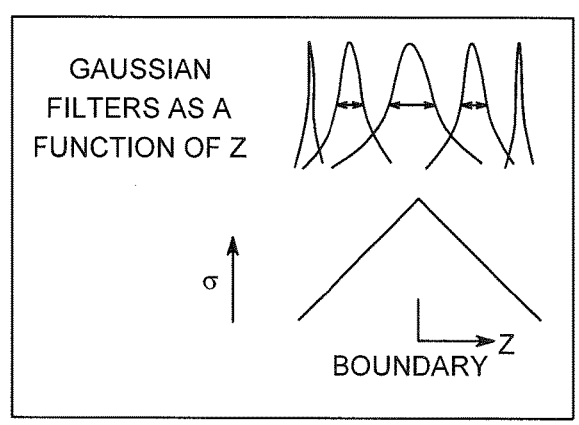
FIG. 8 illustrates triangle weights of a Gaussian filter as a function of Z.

The next step is to generate a function, which has a maximum value of unity and decreases to have a value of zero. These weights are then multiplied by the standard deviation in the z direction such that the maximum standard deviation of the blurring kernel tapers as shown schematically in FIG. 8. In the preferred implementation the z filtering operation is 1D and the same filter may be used for all pixels in the image regardless of the in-plane position. However additional filtering in the in-plane directions could be incorporated as well.

The 1D filtering calculations are performed on a slice by slice basis but in another implementation could just as well be split to be on a pixel by pixel basis. The smoothing filter additionally may have a weight based on the similarity of the image values rather than just the geometrical distance. This type of weight is commonly used image processing and is normally referred to as a bilateral filter. This step is included, in one example, so as not to induce artifacts in the lung window due to contrast enhanced vessels which may be more attenuating than there surrounding lung parenchyma. The result from this step is that the number of slices (assuming they exist from the boundary location) have been processed and are referred to in the high level flow diagram as $I_{ZS}$.

The next step, step 704 of FIG. 7, is to take the difference between the filtered version and the original to isolate the changes that we would like to make to the output image volume. After the difference has been taken the images will be referred to as $I_{diff}$. The difference image may have high frequency information in the z direction as a discontinuity in z will be blended out after the smoothing operation. High frequency information in the difference image should be preserved in the final image and thus the difference image is not filtered in the z direction. However, a low pass filter is performed in-plane at step 706. In the first implementation this is accomplished with a 2D Fourier transform, which includes multiplication by a smooth vessel exclusion mask and an inverse 2D Fourier transform. The final step 708 of the chain is to subtract the difference image which has been low-pass filtered in-plane $I_{LP}$ from the original image $I_{in}$. In this way the noise will not be reduced in the blended region so that the texture will be more uniform in the final output image $I_{out}$. Additionally, high in-plane frequency components such as the edges of vessels will not be affected by this image space z filter operation.

To ensure that no diagnostic information within the coronary arteries is sacrificed at the boundaries by applying a filtering operation in the z direction, a vessel exclusion mask is included in the second pass debanding operation. This vessel exclusion mask is defined on a slice by slice basis and is only calculated for the slices where the second pass debanding is being applied. The vessel mask exclusion logic enables an adaptive approach that avoids filtering in the vicinity of the vessels, allowing an approach that increases image quality for the physician or user without compromise to the vessel/vascular information content. The model used here is that of a line traversing the plane of interest, which is then blurred with a Gaussian function in both the direction parallel and perpendicular to the vessel segment which intersects the given plane of interest.

The assumption is that the vessel points are stored in an array with convention [x_center, y_center, z_center, x_direction_unit_vector, y_direction_unit_vector, z_direction_unit_vector], and unless otherwise specified the units described here are in units of image pixel, as the conversion from mm is expected to occur prior to this step. For each slice in the blending region, first a vessel exclusion mask is initialized.

The vessel exclusion mask is built up from a series of 2D footprints. To avoid discontinuities in z, for any given plane the 2D footprints will be calculated for neighboring slices as well, and a weighted sum will be used to combine in order to generate the mask for the given image slice. The range of the slices that will contribute to a given slice range between a minimum and a maximum that are based on respective max and min values corresponding from the center slice to the edge of the mask. Each of the contributing slices is looped over to get the current mask z smooth weight.

Subsequently, all of the points which intersect the given plane are found from the list of all vessel centerline points. The effective size of each potential footprint is calculated based on the in-plane distance, so that each centerline point does not use exclusion mask calculations in the complete mask. Then the points of interest which intersect this given plane are looped over points of interest, and the center position of each vessel point for both x and y coordinates can be extracted, and then the in-plane extent of the vessel is calculated, after checking for the special case where the vessel is completely in plane to ensure that division by zero errors do not occur.

Here the length of the in-plane segment is first calculated by adding the x and y components in quadrature, and then the in plane distance of a given segment is computed (assuming that the original unit vectors are in an absolute distance coordinate system), a conversion is used for the aspect ratio of the sampling used in the given volume. After the length of the vessel intersection is computed the direction parallel to the vessel (in this axial slice) is computed. An angle alpha ($\alpha$) is 0 at the x axis and positive convention is in the counterclockwise direction.

The blurring parallel to the vessel and perpendicular to the vessel are calculated in units of pixels, and then the blurring value associated with the maximum extent of the vessel ($\sigma_{max}$) is also calculated which ensures that a sharp transition in the exclusion mask does not occur. Then a general two dimensional elliptical Gaussian function is used to define the effective vessel exclusion mask.

After completing the loop over all vessel crossing points and all the neighborhood updates and the loop over all the contributing slices, it is ensured that the map does not have any values of more than unity, which would occur when the footprints of two neighboring vessels overlap.

Additionally, for some reconstruction techniques that blend image data across heart cycles, the preferred embodiment is able to leverage the unblended data (where available) for the vessel registration processing, for increasing image quality. While debanding can be interactively applied by the user, conceptually the computations could also be done in an automated, batched processed fashion. In one embodiment, this batch processing could be included as an additional component within the coronary motion correction subsystem itself.

Figure 9:
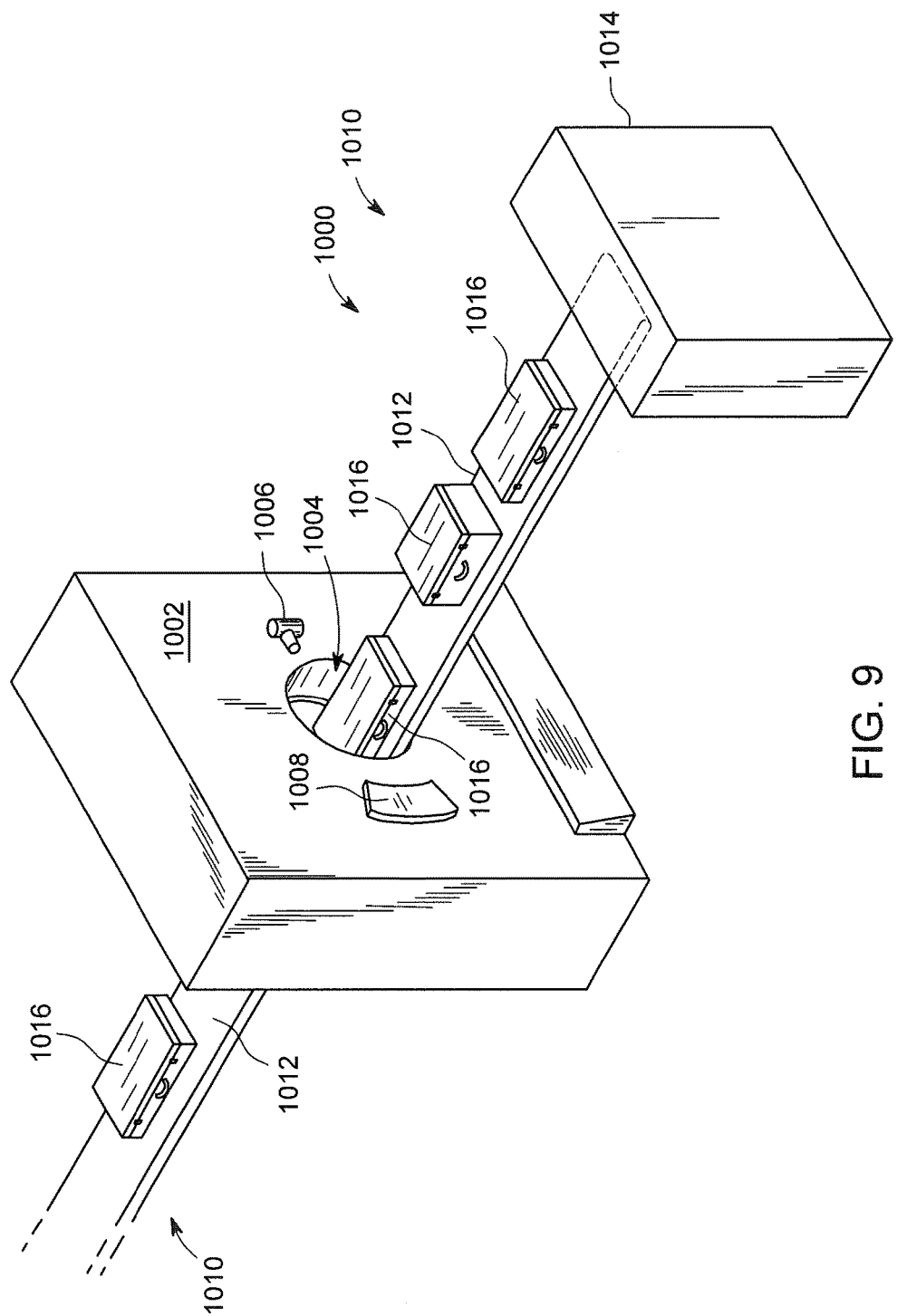
FIG. 9 is a pictorial view of a CT system for use with a non-invasive package inspection system according to an embodiment of the invention.

Referring now to FIG. 9, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

A technical contribution for the disclosed method and apparatus is that it provides for a computer-implemented apparatus and method of diagnostic imaging and, more particularly, to an improved method of post processing reconstructed CT images to improve vessel mis-registration and greyscale de-banding between slabs within a CT image.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, a CT system includes a gantry having a rotatable base and having an opening for receiving an object to be scanned, an x-ray source, a CT detector, and a computer programmed to detect a mis-registration at a slab boundary between a first slab and a second slab of a reconstructed image, quantify an amount of mis-registration at the slab boundary, and adjust the reconstructed image at the slab boundary based on the quantification.

According to another embodiment, a method of CT imaging includes detecting a mis-registration between a first slab and a second slab of a reconstructed image, quantifying an amount of mis-registration between the first and second slabs, and adjusting the reconstructed image in the first and second slabs based on the quantification.

According to yet another embodiment, a non-transitory computer-readable medium tangibly embodying computer-executable instructions that cause the computer to detect a mis-registration at a slab boundary between first and second slabs of a reconstructed image, quantify an amount of mis-registration at the slab boundary, and adjust the reconstructed image at the slab boundary based on the quantification.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the invention has been described in detail in connection with only a limited number of embodiments, it should be readily understood that the invention is not limited to such disclosed embodiments. Rather, that disclosed can be modified to incorporate any number of variations, alterations, substitutions or equivalent arrangements not heretofore described, but which are commensurate with the spirit and scope of the invention. Furthermore, while single energy and dual-energy techniques are discussed above, that disclosed encompasses approaches with more than two energies. Additionally, while various embodiments of the invention have been described, it is to be understood that disclosed aspects may include only some of the described embodiments. Accordingly, that disclosed is not to be seen as limited by the foregoing description, but is only limited by the scope of the appended claims.

What is claimed is:

1. A CT system comprising:
   a gantry having a rotatable base and having an opening for receiving an object to be scanned;
   an x-ray source;
   a CT detector; and
   a computer comprising processing circuitry configured to:
   detect a mis-registration at a slab boundary between a first slab and a second slab of a reconstructed image, wherein the first slab is a reconstructed image of a plurality of slices of imaging data obtained during a first heartbeat, and the second slab is a reconstructed image of a plurality of slices of imaging data obtained during a second heartbeat;
   quantify an amount of mis-registration at the slab boundary by quantifying a vector in an axial plane at the slab boundary; and
   adjust the reconstructed image at the slab boundary based on the quantification by applying a compensation vector to a set of image slices on both sides of the slab boundary, wherein a weight applied to the compensation vector decreases as distance from the slab boundary increases such that effective compensation decreases away from the slab boundary.

2. The CT system of claim 1, wherein the processing circuitry is further configured to:
   identify the slab boundary between the first and second slabs;
   quantify the amount of mis-registration based on a track of a centerline of a vessel on each side of the slab boundary; and
   adjust the reconstructed image based on an offset of the centerline across the slab boundary.

3. The CT system of claim 2, wherein the processing circuitry is configured to determine the offset of the centerline by:
   1) computing two points as an intersection of the centerline with two adjacent planes; and
   2) maximizing a cross-correlation metric centered about the two points.

4. The CT system of claim 3, wherein the processing circuitry is configured to compute a normal displacement between slices at the slab boundary, split the displacement in two, and apply respective splits as shifts to the vessel on either side of the slab boundary.

5. The CT system of claim 4, wherein the processing circuitry is configured to apply the shifts to subsequent slices within each slab in decreasing amounts in slices on either side of the slab boundary.

6. The CT system of claim 5, wherein the processing circuitry is configured to decrease the amounts in slices on either side of the slab boundary in one of a linear, polynomial, power, and logarithmic function.

7. The CT system of claim 1, wherein the processing circuitry is configured to smooth a gray scale between the first and second slabs at the slab boundary by being configured to:
   input an unfiltered volume to a smoothing filter in a z dimension to generate a filtered volume;
   determine a difference image between the filtered volume and the unfiltered volume;
   apply a low-pass filter in-plane to the difference image to obtain a low-pass filter image; and
   subtract the low-pass filter image from the unfiltered volume to generate a blended region.

8. A method of CT imaging, comprising:
   detecting a mis-registration between a first slab and a second slab of a reconstructed image, wherein the first slab is a reconstructed image of a plurality of slices of imaging data obtained during a first heartbeat, and the second slab is a reconstructed image of a plurality of slices of imaging data obtained during a second heartbeat;

quantifying an amount of mis-registration between the first and second slabs by quantifying a vector in an axial plane at the slab boundary; and adjusting the reconstructed image in the first and second slabs based on the quantification by applying a compensation vector to a set of image slices on both sides of the slab boundary, wherein a weight applied to the compensation vector decreases as distance from the slab boundary increases such that effective compensation decreases away from the slab boundary.

9. The method of claim 8, further comprising:

identifying the slab boundary between the first and second slabs;

quantifying the amount of mis-registration based on a track of a centerline of a vessel on each side of the slab boundary; and adjusting the reconstructed image based on an offset of the centerline across the slab boundary.

10. The method of claim 9, further comprising determining the offset of the centerline by:

1) computing two points as an intersection of the centerline with two adjacent planes; and
2) maximizing a cross-correlation metric centered about the two points.

11. The method of claim 10, further comprising:

computing a normal displacement between slices at the slab boundary;

splitting the displacement in two; and applying respective splits as shifts to the vessel on either side of the slab boundary.

12. The method of claim 11, further comprising applying the shifts to subsequent slices within each slab in decreasing amounts in slices on either side of the slab boundary, and decreasing the amounts in slices on either side of the slab boundary in one of a linear, polynomial, power, and logarithmic function.

13. The method of claim 8, further comprising smoothing a gray scale between the first and second slabs at the slab boundary with the steps of:

inputting an unfiltered volume to a Gaussian filter in a z dimension to generate a filtered volume;

determining a difference image between the filtered volume and the unfiltered volume;

applying a low-pass filter in-plane to the difference image to obtain a low-pass filter image; and subtracting the low-pass filter image from the unfiltered volume to generate a blended region.

14. A non-transitory computer-readable medium tangibly embodying computer-executable instructions that cause the computer to:

detect a mis-registration at a slab boundary between first and second slabs of a reconstructed image, wherein the first slab is a reconstructed image of a plurality of slices of imaging data obtained during a first heartbeat, and the second slab is a reconstructed image of a plurality of slices of imaging data obtained during a second heartbeat;

quantify an amount of mis-registration at the slab boundary by quantifying a vector in an axial plane at the slab boundary; and adjust the reconstructed image at the slab boundary based on the quantification by applying a compensation vector to a set of image slices on both sides of the slab boundary, wherein a weight applied to the compensation vector decreases as distance from the slab boundary increases such that effective compensation decreases away from the slab boundary.

15. The non-transitory computer-readable medium of claim 14, wherein the computer is further caused to:

identify the slab boundary between the first and second slabs;

quantify the amount of mis-registration based on a track of a centerline of a vessel on each side of the slab boundary; and adjust the reconstructed image based on an offset of the centerline across the slab boundary.

16. The non-transitory computer-readable medium of claim 15, wherein the computer is further caused to:

determine the offset of the centerline by:

1) computing an intersection of two points; and
2) maximizing a cross-correlation metric centered about the two points;

compute a normal displacement between slices at the slab boundary, split the displacement in two, and apply respective shifts to the vessel on either side of the slab boundary;

apply the respective splits to subsequent slices within each slab in decreasing amounts in slices on either side of the slab boundary; and decrease the amounts in slices on either side of the slab boundary in one of a linear, polynomial, power, and logarithmic function.

17. The non-transitory computer-readable medium of claim 14, wherein the computer is caused to smooth a gray scale between the first and second slabs at the slab boundary by being programmed to:

input an unfiltered volume to a Gaussian filter in a z dimension to generate a filtered volume;

determine a difference image between the filtered volume and the unfiltered volume;

apply a low-pass filter in-plane to the difference image to obtain a low-pass filter image; and subtract the low-pass filter image from the unfiltered volume to generate a blended region.

* * * * *